United States Patent [19]

Mann

[11] 4,232,124
[45] Nov. 4, 1980

[54] METHOD OF PRODUCING PLASMINOGEN ACTIVATOR

[76] Inventor: George F. Mann, 117 Venner Rd., London, England, SE26

[21] Appl. No.: 32,218

[22] Filed: Apr. 23, 1979

Related U.S. Application Data

[63] Continuation of Ser. No. 839,433, Oct. 5, 1977, abandoned.

[51] Int. Cl.³ .......................... C12N 9/72; C12N 9/48
[52] U.S. Cl. ..................................... 435/212; 435/215
[58] Field of Search ........................ 435/212, 215, 217

[56] References Cited

U.S. PATENT DOCUMENTS

| | | | |
|---|---|---|---|
| 3,128,228 | 4/1964 | Michl | 195/1.8 |
| 3,904,480 | 9/1975 | Hull et al. | 195/66 B |
| 3,930,945 | 1/1976 | Lewis | 195/1.7 |

OTHER PUBLICATIONS

Bernick et al., The Journal of Clinical Investigation vol. 48 (1969) pp. 1740-1753.

Barlow et al. "Production of Plasminogen Activator by Tissue Culture" in Proteases and Biological Control, Cold Spring Harbor Conference on Cell Proliferation vol. 2, 1975 pp. 325-331.

*Primary Examiner*—Lionel M. Shapiro
*Attorney, Agent, or Firm*—Fidelman, Wolffe & Waldron

[57] ABSTRACT

Production of plasminogen activator from human diploid lung cells through cultivation in an aqueous nutrient medium containing an inducer of activator production.

Lactalbumin hydrolysate is an active inducer, and is used in 0.1–1.0% w/v concentration in the medium.

6 Claims, No Drawings

METHOD OF PRODUCING PLASMINOGEN ACTIVATOR

This is a continuation of application Ser. No. 839,433 filed Oct. 5, 1977, now abandoned.

The present invention is directed to a method for obtaining plasminogen activator, the enzyme which converts plasminogen to plasmin.

BACKGROUND OF THE INVENTION

Urokinase, the well known plasminogen activator produced by renal cells and urinary tract is excreted in the urine and has been the subject of much interest for possible use as a medicament against sudden fibrinolytic disturbances such as thromboembolism.

One major set of difficulties hindering wide spread employment of urokinase are the problems encountered in the recovery thereof. Human urine, the first recognized source of urokinase contains a low proportion of the enzyme, and therefore human urine for source material purposes offers extreme logistic problems as well as concern that some of the urine donors might also be excreting viruses or other detrimental substances in the urine.

Human kidney cells cultured in vitro, are another recognized source of plasminogen activator. Here too, the yield is relatively low, although yield improvement techniques (c.f. U.S. Pat. Nos. 3,930,945 and 3,904,480 for example) have resulted in limited availability of the kidney cell product.

Since activators derived from transformed, heteroploid or continuous cell lines are not acceptable for production of pharmaceutical products due to possible presence of oncogenic agents and nucleic acid fragments in the products, the normal embryonic kidney cells constitute heretofore the best source material for plasminogen activator. However, normal human embryonic kidney cell cultures have a limited in-vitro life span (20 population doublings) and a supply of fresh embryonic kidney cells is required at frequent intervals. Human embryo kidney is of limited availability, closely controlled by government regulations in most countries. Universally, obtaining viable (embryo) kidney cells involves emotive questions. Whether normal embryonic kidney cells can ever be obtained in the numbers and regularity required to sustain large scale production of plasminogen activator is open to serious question. Nonetheless, heretofore kidney cells cultured in vitro represented the best hopes of the art as source of urokinase in usable quantities.

In the early 1960's Dr. L. Hayflick of the Wistar Institute developed strains of normal human lung cells. These cells, of fibroblastic morphology and exhibiting normal diploid karyotype, enter senescence after 40–60 population doublings. By this method, a pool of cells derived from the lung tissue of a single normal foetus can be screened for the presence of adventitious agents, normal karyotype etc. If satisfactory, this pool can be passaged through 30 further population doublings for the production of biological products such as vaccines. This system gives very large culture areas and has proved extremely satisfactory in the production of polio, measles, mumps, rubella and other vaccines. At least two such cell types have received official approval (by WHO) for the production of biological products, (i.e. MRC-5 and WI-38) and others are under development (eg IMR-90).

STATEMENT OF THE INVENTION

It has now been discovered that human diploid lung cells cultivated in the presence of an inducer for production of plasminogen activator elaborate recoverable quantities of this substance. Lactalbumin hydrolysate is an active inducer.

The great longevity of normal human lung cell strains makes the diploid cell a reliable cell source material for production of plasminogen activator by in vitro tissue cell culture techniques. In addition, the diploid lung cell source material has some other advantages over the kidney cell source material.

DETAILED DESCRIPTION OF THE INVENTION

In the production of plasminogen activator and other substances by culture of mammalian cells, two stages are normally required, i.e. multiplication of the cells in a nutrient medium containing serum, followed by medium change and a maintenance stage for production of the desired substance by the cell culture. In the instance of diploid cells, no serum or plasma is required in the nutrient medium at the maintenance stage. All media contain a mixture of salts, amino acids, vitamins, pH indicator and frequently purines, pyrimidines, etc. Media requirements for in vitro tissue cell cultures are now well known to the art and need not be described in detail herein.

Under the cultivation circumstances normally employed for diploid cells, e.g. vaccine production, very low levels of plasminogen activator (i.e. urokinase) are elaborated. For instance, using MRC-5 cells grown on a solid substratum and maintained on a standard maintenance medium (#199) very low levels of plasminogen activator were detected in the course of routine tests. These levels were very close to the test baseline and might have been discounted if the observation had not been repeated a number of times and on more than one diploid lung cell strain. It was noted also that yield was not materially related to environmental conditions such as pH and cultivation temperature, or to incubation time. A small increase was found when osmolality was raised within the physiological range. The test work indicated that elaboration of plasminogen activator might be limited by nutritional factors.

It has now been discovered that during cultivation of diploid lung cells in the presence of a nutritional supplement, the cells adapted to production of plasminogen activator increasing yield of the enzyme in the medium to recoverable proportions. As intended herein recoverable proportions are defined as urikonase levels exceeding 100 CTA units/ml. The best inducer of nutritional factor discovered by the inventor herein is lactalbumin hydrolysate. Serum, e.g. foetal calf serum also has been found to increase the plasminogen activator titre in the nutrient medium but to a much lesser extent.

According to preferred practice of this invention, cultivation is carried out with 0.1–2.5% of lactalbumin hydrolysate in the growth and/or maintenance medium, which medium may otherwise be a standard tissue culture medium such as those heretofore employed with diploid cells for production of vaccines, including for example Eagles formulations. However, if the growth medium formulation for cell growth does not include human equine, bovine or porcine, etc. serum, presence of serum therein is advantageous. Up to 20% v/v of mammalian serum or plasma in the growth medium is contemplated. Desirably serum is absent from the maintenance medium.

Recovery of the plasminogen activator or urokinase from the maintenance culture medium may be carried out according to practices heretofore employed for recovery from kidney cell culture medium, and from urine and therefore need not be detailed here, c.f. Barlow, G. H. (1976) Methods in Enzymology 45 P+B 239-244; Arstedt and Holmberg L (1976) Nature 261 595-597; Kandall Pye et al (1977) In Thrombosis and Urikinase, Editors Paoletti and Sherry. Academic Press pp. 43-58, and U.S. Pat. Nos. 3,957,582; 4,010,074.

Other attributes of the diploid cells, besides relative availability, make them advantageous source materials for urokinase production. The diploid lung cells elaborate little if any other proteinase activities. Kidney cells were found to elaborate proteinase activity other than the urokinase.

Multiple harvests of activator from the culture medium can be carried out for more than one month, with high levels of activator present in all harvests.

A particular advantage of the diploid cells as source material for urokinase production is that any established strain recognized as safe for vaccine production purposes can be employed. In addition the growth and the maintenance cultivation techniques employed in production of vaccines from diploid lung cells are directly applicable to production of plasminogen activator and their use is contemplated herein.

The concentration of lactalbumin hydrolysate in the culture medium should be in a preferred range of 0.1-1.0% w/v. Greater concentrations were found to reduce longevity of the cell line.

The particular fractions of the lactalbumin hydrolysate which induce production of the activator are not known. However, studies carried out with lactalbumin hydrolysates fractionated by dialysis indicate that the inducing factors are contained in the dialysable fraction and are therefore of low molecular weight.

For further understanding of the practice of this invention reference is made to the following examples.

EXAMPLE 1

Qualitative Production of Plasminogen Activator and Proteinase by Cells in Vitro Specimens of numerous cell types (see table 1) propagated in Falcon flasks were resuspended in Eagles basal medium (described in Grand Island's Biological Catalogue) and seeded into the wells of a multi-welled trays (Limbro) at 200,000 cells/well in 1 ml medium. Cultures were incubated overnight at 36° C. Resulting confluent cultures were washed and overlayed with 199 medium. Medium for one set of cultures contained 0.25% w/v skimmed milk (for detection of proteinase). Medium for another set of cultures, contained both 0.25% skimmed milk and human serum at 1:30 as a source of plasminogen (for detection of activator). Following further incubation at 36° C., the following results were obtained:

TABLE I

| Cell Type | | Plasminogen Activator | Protease |
|---|---|---|---|
| Designation | Source | | |
| Diploid strains | | | |
| MRC-5 PDL 31 | Human embryo lung | + | − |
| MRC-5 PDL 22 | (diploid strains) | + | − |
| HEL-Ki PDL 3 | | + | − |
| WI-38 PDL 28 | | + | − |
| IMR-90 PDL 26 | | + | − |

TABLE I-continued

| Cell Type | | Plasminogen Activator | Protease |
|---|---|---|---|
| Designation | Source | | |
| Continuous lines | | | |
| HEp2 | Human carcinoma | − | − |
| L 929 | Mouse | − | − |
| Hep.M | Hepatoma-human | − | − |
| Vero | Monkey kidney | − | − |
| BHK 21 | Baby hamster kidney | + | − |
| LLC-MK$_2$ | Monkey Kidney | + | ± |
| Primary/Secondary Cultures | | | |
| Monkey Kidney | Rhesus (2°) | + | + |
| Human embryo kidney | Primary | + | + |
| Mouse fibroblasts | Mouse embryos (2°) | + | − |

+Indicates clearing of milk with absence of TCA precipitable protein.

EXAMPLE 2

Titration of Activator and Plasmin from Qualitative Experiments

Duplicate cell cultures in medium 199 were incubated with and without plasminogen; after 3 days at 36° C., activated plasmin and activator respectively were titrated. In control tests, a plasmin titre of 1:4 was found to represent complete activation of the plasminogen present in the system.

The results are tabulated below:

TABLE II

| Cell Type | Plasminogen Activator Titre' /0.1ml. | Activated Plasmin Titre /0.1ml. |
|---|---|---|
| MRC-5 P31 | 1 | 4 |
| LLC-MK$_2$ | 4 | 4 |
| MK | 16 | 4 |

'Reciprocal of dilution showing digestion of milk in presence of plasminogen after 3 days at 36° C.

EXAMPLE 3

Effect of Incubation Time on Activator Production by MRC-5 Cells in 199 Medium

Replicate cultures of MRC-5 cells at P32 (passage 32) were washed and incubated in 199 medium at 36° C. Medium was changed and samples taken from duplicate bottles at the times indicated. Cell activator titre was determined after freezing and thawing of the culture in fresh 199 medium.

The results are tabulated below:

TABLE III

| Incubation | | Activator Titre/0.1ml. | |
|---|---|---|---|
| Days | Time (hours) | Medium | Cells |
| 0-1 | 24 | 10 | 4 |
| 1-2 | 24 | 8 | 2 |
| 2-3 | 24 | 8 | 3 |
| 3-4 | 24 | 8 | 3 |
| 0-1 | 24 | 10 | 4 |
| 0-2 | 48 | 8 | 4 |
| 0-3 | 72 | 12 | 2 |
| 0-4 | 96 | 8 | NR |

EXAMPLE 4

Influence of Medium pH and Osmolality on Activator Production by MRC-5 Cells in Medium 199

The procedure of Example 3 was followed with variation in pH and osmalality for 4 days. The results are tabulated below:

TABLE IV

| Medium | | Activator Titre/0.1ml | |
|---|---|---|---|
| pH | Osmolality* | Medium | Cells |
| 7.2 | 1 | 16 | 2 |
| 7.6 | 1 | 10 | 2 |
| 7.8 | 1 | 16 | 2 |
| 7.6 | 0.6 | 4 | 2 |
| 7.6 | 1.0 | 10 | 2 |
| 7.6 | 1.5 | 32 | 8 |

*Relative to normal 199 medium (Gibco E11).

EXAMPLE 5

Production of Plasminogen Activator in 199 Medium at Different Temperatures

The procedure of Example 3 was followed with a cultivation period of 4 days at different cultivation temperatures. The results are tabulated below:

TABLE V

| Incubation Temperature °C. | Medium Activator Titre/0.1ml |
|---|---|
| 28° C. | 8 |
| 33° C. | 8 |
| 36° C. | 8 |

EXAMPLE 6

Effect of Additives on Activator Production by MRC-5 Cells

Following the procedure of Example 3 with 4 days cultivation, the affect of nutrient additives (to 199 medium) was ascertained. The results being tabulated below:

TABLE VI

| Additive | Activator Medium | Titre/0.1ml Cells |
|---|---|---|
| None | 8 | 3 |
| 2% Foetal Calf Serum | 32 | 4 |
| 0.25% Lactalbumin Hydrolysate | 64 | 32 |
| 0.1% Bovine Albumin (Cohn F + V) | 12 | 2 |

EXAMPLE 7

Dynamics of Activator Production by MRC-5 Cells With Lactalbumin Hydrolysate (LAH)

Replicate cultures of MRC-5 cells at P33 were washed and overlayed with medium and incubated at 36° C. Samples were taken at various times and frozen. All samples were titrated in parallel, medium changed after 8 days. The test details and results are tabulated below:

TABLE VII

| Medium and Relative Osmolality* | Lactalbumin Hydrolysate %w/v | Medium Activator Titre' Day | | | | Notes |
|---|---|---|---|---|---|---|
| | | 1 | 2 | 4 | 8 | |
| 199 0.5x | None | 2 | 2 | 2 | 2 | Cultures |
| | 0.1 | 2 | 4 | 2 | 2 | degener- |
| | 0.2 | 4 | 8 | 4 | 4 | ated at |
| | 0.4 | 4 | 8 | 16 | 8 | day 6. |
| | 0.8 | 8 | 4 | 16 | 16 | |
| 199 1.0x | None | 8 | 8 | 4 | 8 | |
| | 0.1 | 8 | 16 | 64 | 64 | |
| | 0.2 | 16 | 16 | 64 | 128 | |
| | 0.4 | 16 | 32 | 128 | 256 | |
| | 0.8 | 32 | 32 | 64 | 128 | |
| 199 1.5x | None | 4 | 16 | 16 | 32 | |
| | 0.1 | 4 | 16 | 64 | 128 | All |
| | 0.2 | 4 | 16 | 64 | 256 | cultures |
| | 0.4 | 2 | 16 | 64 | 384 | w/LAH |
| | 0.8 | 2 | NR | NR | NR | showed degeneration and precipitation by day 12 |

*Relative to normal 199 medium (GIBCO E11)

EXAMPLE VIII

Human diploid fibroblast cells of the MCR-5 strain were serially propogated in Falcon flasks (by Hayflick's procedures) to give monolayer cultures of an appropriate area and population doubling level for use as a cellular inoculum, (taking care not to exceed the doubling equivilent of ⅔ of the life span of the cells).

Cells from inoculum cultures were resuspended, after treatment with trypsin/versene solution, in Eagles basal medium supplemented with fetal calf serum. These cells were then seeded into further flasks to give four times the culture area from which the inoculum and medium at 0.5 ml/cm$^2$ were incubated at 36° C. in 5% $CO_2$: 95% air for 5 days to give confluent, contriguous cell layers.

At the 5th day, Eagles medium was removed and the monolayers washed with three changes of phosphate buffered saline pH 7.4 to remove residual bovine serum. Cultures were then overlayed with 199 medium containing lactalbumin hydrolysate to 0.5% w/v and at 0.33 ml/cm$^2$ of culture. Control flasks were treated identically, but omitting lactalbumin hydrolysate. Cultures were then re-incubated at 36° C. as above.

Samples were withdrawn at different times for the assay of plasminogen activator and medium was replaced at intervals to ensure adequate provision of nutrient for cell maintenance.

Assays of activator were carried out on all samples (c.f. the method described by Barnett and Baron (1959).

In the presence of lactalbumin hydrolysate, plasminogen activator concentration increases progressively over a four a eight day period as follows:

TABLE VIII(a)

| Labtalbumin Concentration % w/v | Activator/0.1ml of Medium Incubation Time. Days at 36° C. | | | |
|---|---|---|---|---|
| | 1 | 2 | 4 | 8 |
| 0 | 8 | 8 | 4 | 8 |
| 0.5% | 16 | 32 | 128 | 256 |

By medium changes at intervals, multiple harvests of activator were obtained from the cultures as follows:

TABLE VIII(b)

| Period (Days) | Activator/0.1 ml Harvest |
| --- | --- |
| 0–8 | 256 |
| 8–13 | 512 |
| 13–16 | 320 |
| 16–21 | 256 |
| 21–28 | 512 |

What is claimed:

1. A method for producing plasminogen activator which comprises culturing human diploid lung cells in vitro in an aqueous nutrient maintenance medium free of serum containing therein an inducer which enhances production of plasminogen activator by the cells until plasminogen activator content in the nutrient medium exceeds 100 CTA units/ml and thereafter separating nutrient medium from the cells.

2. A method for producing plasminogen activator which comprises culturing human diploid lung cells in vitro in an aqueous nutrient medium containing therein an inducer comprising lactalbumin hydrolysate until plasminogen activator content in the nutrient medium exceeds 100 CTA units/ml and thereafter separating nutrient medium from the cells.

3. A method for producing plasminogen activator which comprises culturing human embryo diploid lung cells in vitro in an aqueous nutrient medium containing therein an inducer comprising lactalbumin hydrolysate in from 0.1–1.0% w/v of the nutrient medium until plasminogen activator content in the nutrient medium exceeds 100 CTA units/ml, thereafter separating nutrient medium from the cells and then recovering the activator from the medium.

4. The method of claim 2 wherein the lactalbumin hydrolysate is from 0.1–1.0% w/v of the nutrient medium.

5. The method of claim 1 wherein the plasminogen activator is thereafter recovered from the medium.

6. The method of claim 3 wherein the medium is changed periodically, whereby multiple harvests of activator are obtained from the same cell culture.

* * * * *